US010206801B2

(12) United States Patent
Eller

(10) Patent No.: US 10,206,801 B2
(45) Date of Patent: Feb. 19, 2019

(54) TRIGGER WIRE ARRANGEMENTS FOR ENDOGRAFTS

(71) Applicant: COOK MEDICAL TECHNOLOGIES LLC, Bloomington, IN (US)

(72) Inventor: Derek Eller, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 373 days.

(21) Appl. No.: 14/971,222

(22) Filed: Dec. 16, 2015

(65) Prior Publication Data

US 2016/0184116 A1     Jun. 30, 2016

Related U.S. Application Data

(60) Provisional application No. 62/097,487, filed on Dec. 29, 2014.

(51) Int. Cl.
*A61F 2/95* (2013.01)
*A61F 2/92* (2013.01)

(52) U.S. Cl.
CPC .............. *A61F 2/95* (2013.01); *A61F 2/92* (2013.01); *A61F 2002/9505* (2013.01); *A61F 2002/9511* (2013.01)

(58) Field of Classification Search
CPC ...... A61F 2/95; A61F 2002/9505; A61F 2/92; A61F 2002/9511

(Continued)

(56) References Cited

U.S. PATENT DOCUMENTS 6,165,210 A * 12/2000 Lau ........................ A61F 2/88
                                                      623/1.12
8,114,145 B2   2/2012   Hartley et al.
(Continued)

FOREIGN PATENT DOCUMENTS

EP    2 471 498 A1   7/2012
GB    2 464 977 A   5/2010
(Continued)

OTHER PUBLICATIONS

Extended European Search Report from corresponding European application No. 15275264.8-1662, 6pgs., dated Jun. 1, 2016.
(Continued)

*Primary Examiner* — Vy Bui
(74) *Attorney, Agent, or Firm* — Brinks Gilson & Lione

(57) ABSTRACT

The present embodiments provide prosthesis deployment systems. In one embodiment, a sleeve has proximal and distal regions and a lumen extending therebetween, and further comprising a first exit aperture, a first entrance aperture, and a second exit aperture. A trigger wire is disposed at least partially within the lumen of the sleeve. A prosthesis has a delivery state and an expanded state, and further has first and second regions. In the delivery state, the trigger wire extends out of the lumen through the first exit aperture of the sleeve, restrains the first region of the prosthesis, reenters the lumen through the first entrance aperture of the sleeve, extends out of the lumen through the second exit aperture of the sleeve, and restrains the second region of the prosthesis.

16 Claims, 4 Drawing Sheets

(58) Field of Classification Search
USPC ................... 623/1.11, 1.12, 1.16, 1.23, 1.36; 606/191, 192, 194, 195, 198
See application file for complete search history.

(56) References Cited

U.S. PATENT DOCUMENTS

| | | |
|---|---|---|
| 2009/0048656 A1 | 2/2009 | Wen |
| 2009/0204202 A1 | 8/2009 | Dierking et al. |
| 2011/0125244 A1 | 5/2011 | Roeder et al. |
| 2011/0288624 A1 | 11/2011 | Roeder |
| 2013/0245742 A1 | 9/2013 | Norris |
| 2014/0277350 A1* | 9/2014 | Melsheimer ............ A61F 2/962 623/1.11 |

FOREIGN PATENT DOCUMENTS

| | | |
|---|---|---|
| WO | WO 2008/140796 A1 | 11/2008 |
| WO | WO 2011/062858 A1 | 5/2011 |

OTHER PUBLICATIONS

Examination Report from corresponding European application No. 15275264.8, 7pgs., dated Apr. 17, 2018.
Examination Report from corresponding European application No. 15275264.8, 5pgs., dated Sep. 27, 2017.

\* cited by examiner

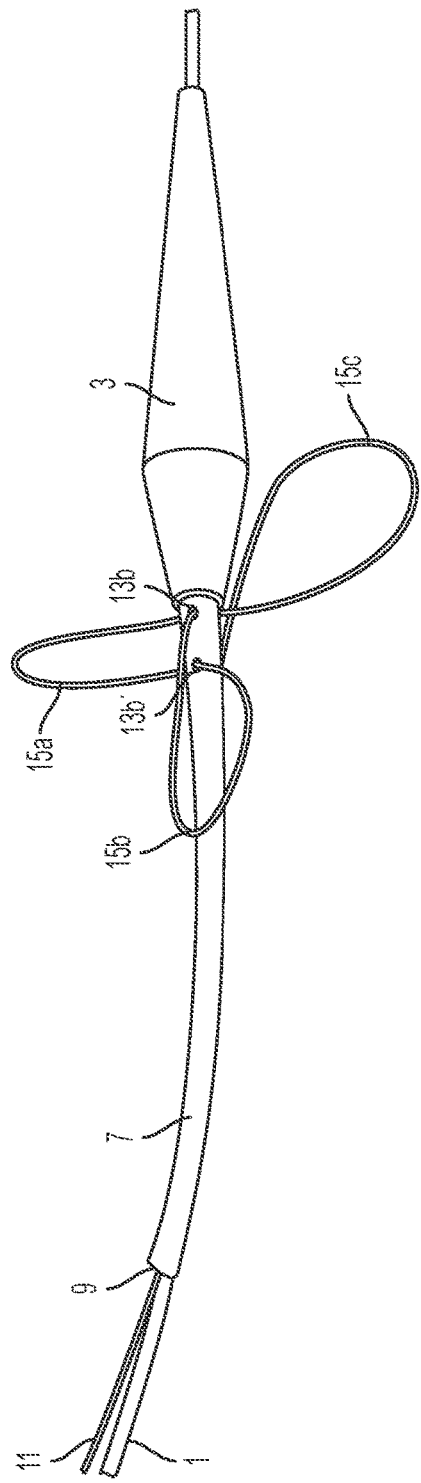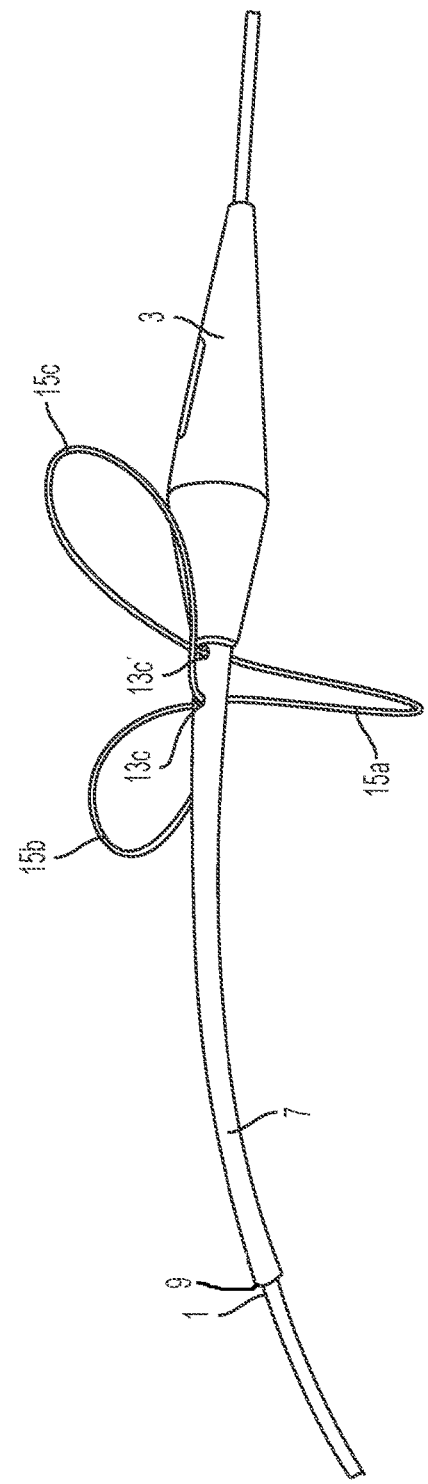

TRIGGER WIRE ARRANGEMENTS FOR ENDOGRAFTS

PRIORITY CLAIM

This invention claims the benefit of priority of U.S. Provisional Application Ser. No. 62/097,487, entitled "Trigger Wire Arrangements for Endografts," filed Dec. 29, 2014, which is hereby incorporated by reference in its entirety.

BACKGROUND

The embodiments relate to a prosthesis deployment system and more particularly to trigger wire arrangements used on such systems to release a prosthesis when it is in a body lumen.

Deployment systems are used to deploy prostheses, for example, prostheses that incorporate self-expanding stents within lumens in the human body. The present embodiments will generally be discussed in relation to the deployment of prostheses within the aorta, but the embodiments are not so limited and may be used for other deployment sites, as well.

In some forms of deployment systems, trigger wires are used to restrain a prosthesis in a particular position on a deployment system or to restrain self-expanding stents of the prosthesis in a retracted state. When multiple trigger wires are used in the deployment systems, the systems are more complex and may restrain prostheses inefficiently or require a larger system profile.

BRIEF SUMMARY

The present embodiments provide prosthesis deployment systems. In one exemplary embodiment, a sleeve has proximal and distal regions and a lumen extending therebetween, and further comprising a first exit aperture, a first entrance aperture, and a second exit aperture. A trigger wire is disposed at least partially within the lumen of the sleeve. A prosthesis has a delivery state and an expanded state, and further has first and second regions. In the delivery state, the trigger wire extends out of the lumen through the first exit aperture of the sleeve, restrains the first region of the prosthesis, reenters the lumen through the first entrance aperture of the sleeve, extends out of the lumen through the second exit aperture of the sleeve, and restrains the second region of the prosthesis.

The deployment system may comprise an inner cannula disposed within the sleeve. In one embodiment, the lumen of the sleeve may be formed in a coaxial space between the inner cannula and the sleeve. In another embodiment, the lumen of the sleeve is coaxial only with the trigger wire.

In the delivery state, the trigger wire may extend both axially and circumferentially within the lumen of the sleeve.

In various examples, the trigger wire may restrain at least three regions of the prosthesis. The trigger wire may reenter the lumen through a second entrance aperture of the sleeve, extend out of the lumen through a third exit aperture of the sleeve, and restrain a third region of the prosthesis.

In certain examples, the prosthesis may comprise at least one stent, and in the delivery state, the trigger wire may engage a first region of the stent after extending out of the lumen through the first exit aperture of the sleeve and before reentering the lumen through the first entrance aperture of the sleeve. The trigger wire may further engage a second region of the stent after extending out of the lumen through the second exit aperture of the sleeve and before reentering the lumen through a second entrance aperture of the sleeve.

The trigger wire may further engage a third region of the stent after extending out of the lumen through a third exit aperture of the sleeve and before reentering the lumen through a third entrance aperture of the sleeve.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like referenced numerals designate corresponding parts throughout the different views.

FIGS. 2a and 2b are side views of a prosthesis deployment system incorporating a trigger wire arrangement, where FIG. 2b is rotated relative to FIG. 2a.

DETAILED DESCRIPTION OF THE DRAWINGS AND THE PRESENTLY PREFERRED EMBODIMENTS

Figure 1:
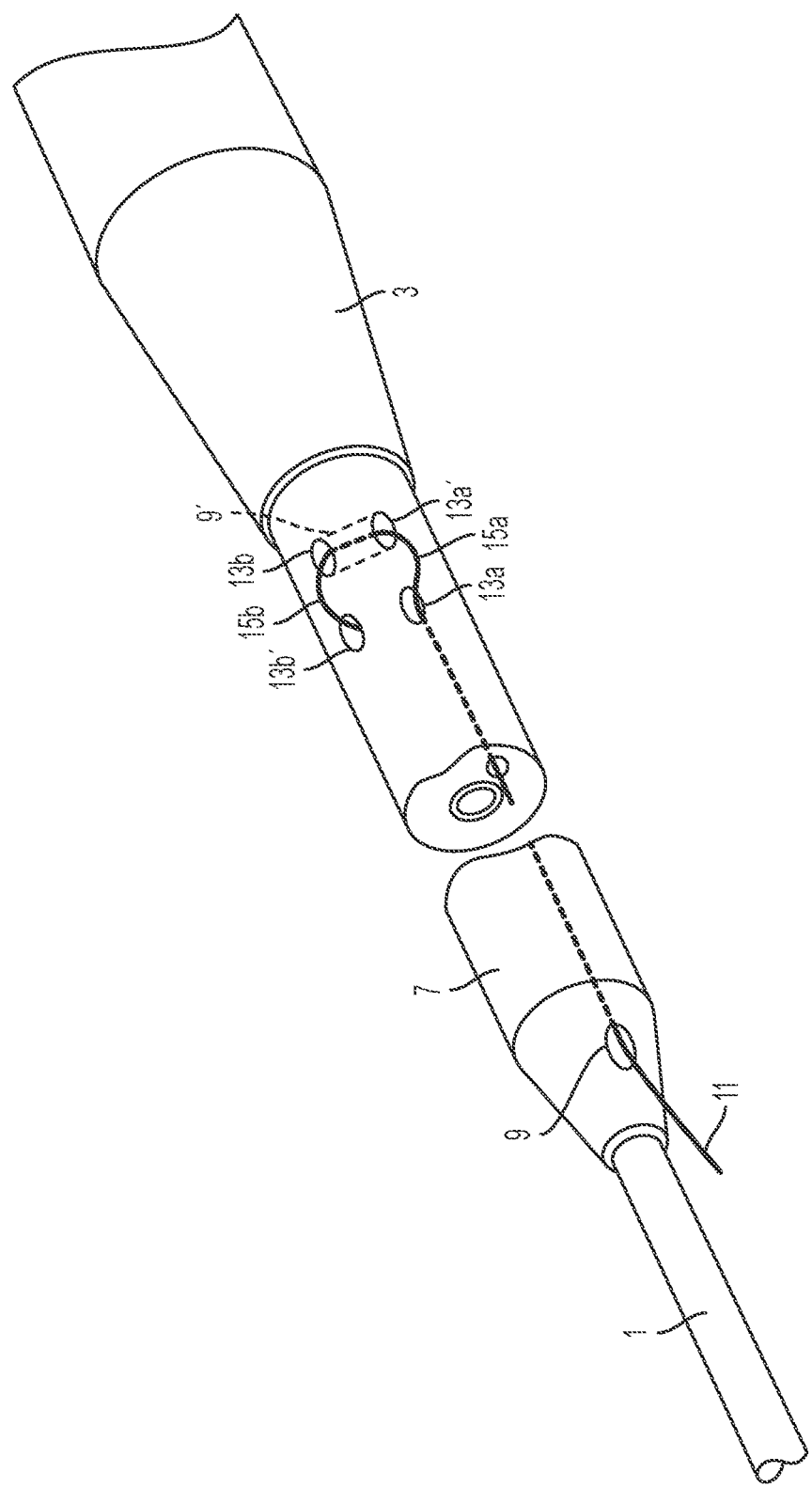
FIG. 1 is a perspective view of part of a prosthesis deployment system, incorporating a trigger wire arrangement, of one embodiment.

In the present application, the term "proximal" refers to a direction that is generally closest to the heart during a medical procedure, while the term "distal" refers to a direction that is furthest from the heart during a medical procedure.

Prosthesis deployment systems are medical devices manipulated by a doctor and used to deploy prostheses, for example, prostheses that incorporate self-expanding stents within lumens in the human body.

In FIGS. 1-4, a part of a prosthesis deployment system is shown and may include an inner cannula 1 which extends the length of the deployment system. A nose cone dilator 3 is coupled to the proximal end of the inner cannula 1. The nose cone dilator 3 may subsequently transition into a smaller diameter at a proximal location, such that the relatively small diameter proximal region allows for atraumatic access and delivery.

A sleeve 7 may extend distally from the nose cone dilator 3 and surround at least a portion of the inner cannula 1. The sleeve 7 may be coaxial with the inner cannula 1 and may include a lumen 9 through which, in use, a trigger wire 11 may pass.

In one embodiment, the lumen 9 of the sleeve 7 may be coaxially between the inner cannula 1 and the sleeve 7, as shown in FIG. 2a. In this embodiment, the trigger wire 11 passes in the annular space that is coaxially in-between the sleeve 7 and the inner cannula 1.

Alternatively, a separate lumen may be formed within the sleeve 7, as shown in FIG. 1. In this alternative, the trigger wire 11 may extend from a conventional trigger wire release mechanism, which is distal to the part of the prosthesis deployment system shown in FIGS. 1-4, through a lumen 9 that is formed within the sleeve 7, e.g., at a location radially offset from the inner cannula 1, as depicted in FIG. 1. In this embodiment, a primary lumen 9 may extend axially along a majority of the length of the sleeve 7, and then one or more discrete lumen sections 9' may be provided between specific apertures of the sleeve 7, such as lumen section 9' that extends circumferentially between a first entrance aperture 13a' and a second exit aperture 13b, as depicted in FIG. 1. In this manner, multiple lumen sections may be provided, as needed, to accommodate the portions of the trigger wire 11 that are selectively disposed beneath the sleeve 7.

Just distal of the nose cone dilator 3, there may be a plurality of apertures 13 in the sleeve 7 extending into the lumen 9. The trigger wire 11 may extend out of the apertures 13 to form a plurality of loops 15 so that the trigger wire 11 may engage a plurality of regions of a stent 23 of a prosthesis 19 (see FIGS. 4a and 4b). The trigger wire 11 then re-enters the lumen 9 of the sleeve 7 via different apertures 13 than the trigger wire 11 exited from.

In previously-known prosthesis deployment systems, each loop may have required a separate trigger wire. Therefore, each stent apex that was restrained by a prosthesis deployment system may have required a separate trigger wire. For example, if a prosthesis was restrained at three places, then three trigger wires may have been used. Each trigger wire may have ran along the length of an inner cannula, within a lumen between an inner cannula and a surrounding sleeve. Each trigger wire may have extended out of an aperture to be disposed around a single stent apex of a prosthesis. Each trigger wire may have reentered a sleeve via a separate aperture, continued proximally along a lumen, and been disposed at or beneath a nose cone dilator in a conventional manner. Alternatively, the trigger wire may end in the lumen itself. As explained below, the present embodiments advantageously utilize the single trigger wire 11 to restrain multiple apices 17 (or other distinct regions) of the stent 23.

Referring to FIGS. 1-2b, the single trigger wire 11, in a delivery state, may run substantially along the length of the inner cannula 1 and the sleeve 7, within the lumen 9 as explained above. The trigger wire 11 may extend out of a first exit aperture 13a to form a loop 15a. The trigger wire 11 may reenter the lumen 9 of the sleeve 7 via a first entrance aperture 13a', run along a portion of a circumference of the lumen 9, and extend out of a second exit aperture 13b to form a loop 15b. This process of reentering the lumen 9 of the sleeve 7, running along a portion of the circumference of the lumen 9, and extending out of the lumen 9 to form another loop 15 may be repeated as many times as necessary to form the desired number of loops 15. Once that number is obtained, the trigger wire 11 may reenter the lumen 9 of the sleeve 7, continue proximally along the lumen 9, and be disposed at or beneath the nose cone dilator 3. In this context, the use of "the lumen 9" may encompass the embodiment of the co-axial lumen 9 between the inner cannula 1 and the sleeve 7 depicted in FIGS. 2a-2b, or alternatively may collectively reference the primary lumen 9 and the discrete lumen sections 9' explained in FIG. 1 above. Alternatively, the trigger wire 11 may end in the lumen 9 itself.

Figure 3:
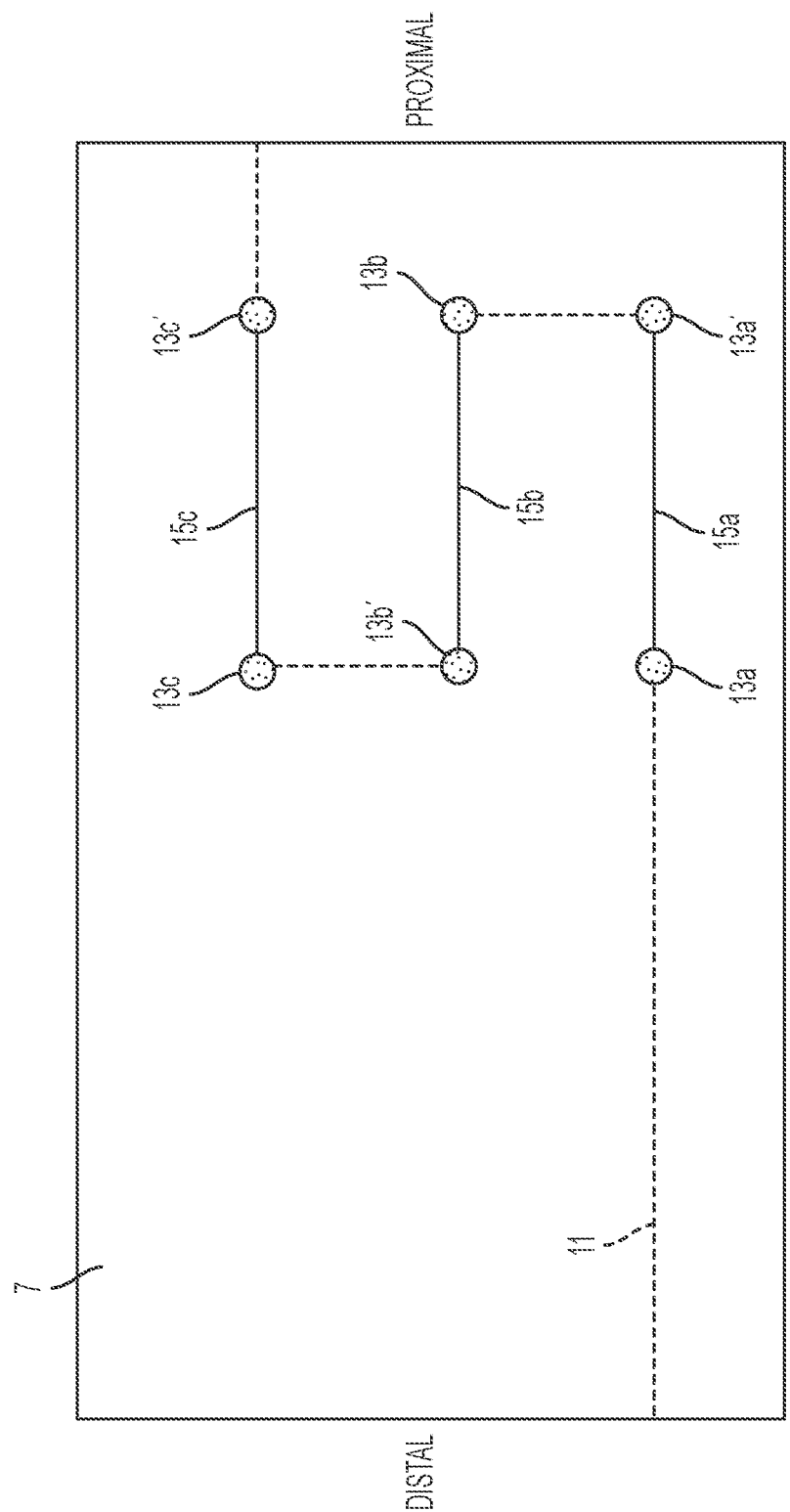
FIG. 3 is a two-dimensional projection of a prosthesis deployment system sleeve and a trigger wire arrangement.

Referring to FIG. 3, the outer rectangle represents the sleeve 7, cut longitudinally down one side and laid flat. The dotted lines represent the trigger wire 11 when it is in the lumen 9 of the sleeve 7, and the solid lines represent the trigger wire 11 when it is outside of the lumen 9 of the sleeve 7. The lines show the path of the trigger wire 11 as it exits and enters the lumen 9 of the sleeve 7 to form the loops 15 and runs along a portion of the circumference of the lumen 9 of the sleeve 7.

The embodiment disclosed above is only one exemplary trigger wire arrangement. The trigger wire 11 exiting and entering the lumen 9 of the sleeve 7 via different apertures 13, the trigger wire 11 running along various portions of the circumference and/or a length of the lumen 9 of the sleeve 7, and other combinations and variations of trigger wire arrangements may be provided.

Figure 4A:
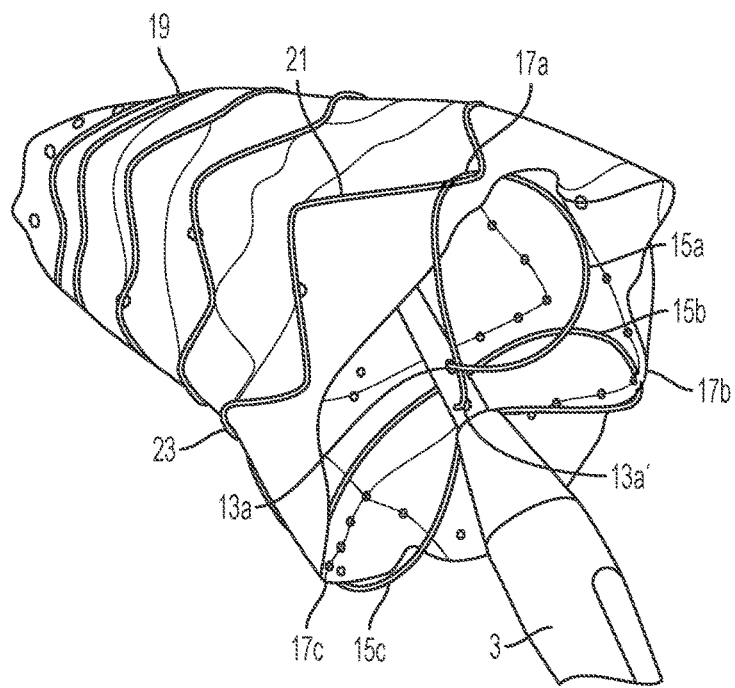
FIGS. 4a and 4b are operational views of a prosthesis deployment system incorporating a trigger wire arrangement.
Figure 4B:
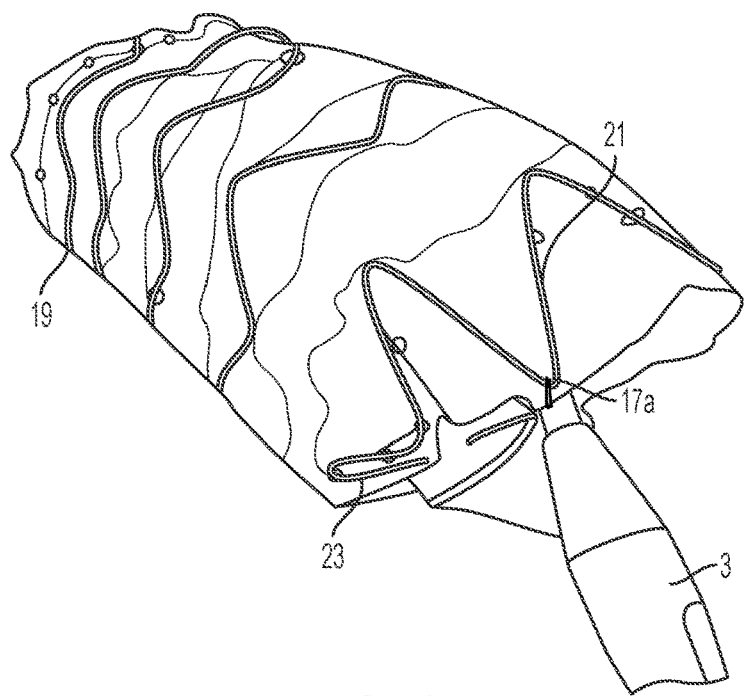

An exemplary prosthesis 19, which is suitable for use with the trigger wire 11, is shown in FIGS. 4a and 4b. The prosthesis 19 may comprise at least one stent 23, which comprises a plurality of struts 21 and apices 17. To restrain multiple apices 17 of the stent 23, the trigger wire 11 may extend out of the first exit aperture 13a to form the loop 15a. The loop 15a may be disposed around the apex 17a of the stent 23 (with or without passing through graft material of the prosthesis 19) and reenter the lumen 9 of the sleeve 7 via the first entrance aperture 13a'. The trigger wire 11 then may run along the length and/or circumference of the lumen 9 and extend out of the second exit aperture 13b to form the loop 15b. The trigger wire 11 in its loop 15b may then be disposed around an apex 17b of the stent 23, and reenter the lumen 9 of the sleeve 7 via a second entrance aperture 13b'. The process of running along the length and/or circumference of the lumen 9, extending out of the lumen 9 to form another loop 15, and being disposed around another apex 17 of the stent 23, and reentering the lumen 9 may be repeated as many times as necessary to restrain the desired amount of apices 17 of the stent 23. FIG. 4b shows the apices 17 of the stent 23 being restrained by the trigger wire 11.

The use of the single trigger wire 11 may serve as an improvement for the deployment of the prosthesis 19. The trigger wire release mechanism may function, in an expanded state, by withdrawing the trigger wire 11 to the distal end of the prosthesis deployment system. The withdrawal of the trigger wire 11 may release the apices 17 of the stent 23. Advantageously, since one trigger wire 11 is used to restrain multiple apices 17 of the stent 23, wire binding or tangling within the lumen 9 is less likely, and less force may be required for trigger wire withdrawal due to the lack of friction between multiple trigger wires. Another advantage associated with the use of one trigger wire 11 is that the apices 17 of the stent 23 may release sequentially, as opposed to simultaneously, which may lead to atraumatic deployment of the prosthesis 19. Lastly, the amount of time, components, and complexity needed for system loading is reduced.

While only one trigger wire 11 is depicted for deploying the stent 23, the trigger wire 11 may be used with at least one other trigger wire if needed. For example, the trigger wire 11 may be used to restrain anywhere from 3-10 discrete sections (apices or otherwise) of the stent 23, and one or more other wires may be used to restrain other discrete sections of the stent 23. In the end, the number of overall trigger wires is still significantly reduced because the trigger wire 11 restrains several apices.

Further, while FIGS. 4a and 4b show the trigger wire 11 restraining proximal regions of the exemplary stent 23, the trigger wire 11 may restrain other regions of the stent 23 or the prosthesis 19 in general. For example, the trigger wire 11 may alternatively restrain central or distally disposed z-stents, or the trigger wire 11 may run axially and circumferentially to restrain multiple different stents, or portions of a single stent, or may restrain other portions of the prosthesis 19 along the proximal, central, and/or distal regions of the prosthesis 19.

Further, while the exemplary stent 23 shown in FIGS. 4a and 4b is z-shaped, it will be appreciated that the trigger wire 11 may restrain stents with different shapes and/or configurations.

In a further alternative embodiment, the sleeve 7 may not be in the form of an elongated tube as depicted, but rather may comprise one or more restraining structures adjacent to the inner cannula 1. The one or more restraining structures may comprise one or more thin strips of material that are adjacent to the inner cannula 1 and keep the trigger wire 11 from moving radially away from the inner cannula 1, while effectively performing the same function as the elongated tube form of the sleeve 7.

While various embodiments have been described, the embodiments are not to be restricted except in light of the attached claims and their equivalents. Moreover, the advantages described herein are not necessarily the only advantages of the embodiments, and it is not necessarily expected that every embodiment will achieve all of the advantages described.

The invention claimed is:

1. A prosthesis deployment system comprising:
   a sleeve having proximal and distal regions and a lumen extending therebetween, and further comprising a first exit aperture, a first entrance aperture, and a second exit aperture;
   a trigger wire disposed at least partially within the lumen of the sleeve; and
   a prosthesis having a delivery state and an expanded state, and further having first and second regions,
   where, in the delivery state, the trigger wire extends out of the lumen through the first exit aperture of the sleeve, restrains the first region of the prosthesis, reenters the lumen through the first entrance aperture of the sleeve, extends out of the lumen through the second exit aperture of the sleeve, and restrains the second region of the prosthesis; and wherein the prosthesis comprises a stent and a graft.

2. The prosthesis deployment system of claim 1, further comprising an inner cannula disposed within the sleeve, wherein the lumen of the sleeve is formed in a coaxial space between the inner cannula and the sleeve.

3. The prosthesis deployment system of claim 1 wherein the lumen of the sleeve is coaxial only with the trigger wire.

4. The prosthesis deployment system of claim 1 wherein, in the delivery state, the trigger wire extends both axially and circumferentially within the lumen of the sleeve.

5. The prosthesis deployment system of claim 1 where, in the delivery state, the trigger wire restrains at least three regions of the prosthesis.

6. The prosthesis deployment system of claim 5 wherein, in the delivery state, the trigger wire further reenters the lumen through a second entrance aperture of the sleeve, extends out of the lumen through a third exit aperture of the sleeve, and restrains a third region of the prosthesis.

7. The prosthesis deployment system of claim 1, wherein the prosthesis comprises at least one stent, and wherein, in the delivery state, the trigger wire engages a first region of the stent after extending out of the lumen through the first exit aperture of the sleeve and before reentering the lumen through the first entrance aperture of the sleeve.

8. The prosthesis deployment system of claim 7, wherein, in the delivery state, the trigger wire further engages a second region of the stent after extending out of the lumen through the second exit aperture of the sleeve and before reentering the lumen through a second entrance aperture of the sleeve.

9. The prosthesis deployment system of claim 8 wherein, in the delivery state, the trigger wire further engages a third region of the stent after extending out of the lumen through a third exit aperture of the sleeve and before reentering the lumen through a third entrance aperture of the sleeve.

10. A prosthesis deployment system comprising:
    a sleeve having proximal and distal regions and a lumen extending therebetween;
    a trigger wire disposed at least partially within the lumen of the sleeve; and
    a prosthesis having a delivery state and an expanded state,
    where, in the delivery state, the trigger wire extends both axially and circumferentially within the lumen of the sleeve and restrains at least two regions of the the prosthesis;
    wherein the sleeve further comprises a first exit aperture, a first entrance aperture, and a second exit aperture and where, in the delivery state, the trigger wire extends out of the lumen through the first exit aperture of the sleeve, restrains a first region of the prosthesis, reenters the lumen through the first entrance aperture of the sleeve, extends out of the lumen through the second exit aperture of the sleeve, and restrains a second region of the prosthesis; and wherein the prosthesis comprises a stent and a graft.

11. The prosthesis deployment system of claim 10, further comprising an inner cannula disposed within the sleeve, wherein the lumen is formed in a coaxial space between the inner cannula and the sleeve.

12. The prosthesis deployment system of claim 10 wherein, in the expanded state, the trigger wire releases the at least two regions of the prosthesis sequentially.

13. The prosthesis deployment system of claim 10 wherein, in the delivery state, the trigger wire further reenters the lumen through a second entrance aperture of the sleeve, extends out of the lumen through a third exit aperture of the sleeve, and restrains a third region of the prosthesis.

14. A prosthesis deployment system comprising:
    a sleeve having proximal and distal regions and a lumen extending therebetween;
    a trigger wire disposed at least partially within the lumen of the sleeve; and
    a prosthesis having a delivery state and an expanded state,
    where, in the delivery state, the trigger wire extends both axially and circumferentially within the lumen of the sleeve and restrains at least two regions of the prosthesis, and
    wherein the prosthesis comprises a stent and a graft, and where, in the delivery state, the trigger wire engages a first region of the at least one stent after extending out of the lumen through a first exit aperture of the sleeve and before reentering the lumen through a first entrance aperture of the sleeve.

15. The prosthesis deployment system of claim 14, where, in the delivery state, the trigger wire further engages a second region of the at least one stent after extending out of the lumen through a second exit aperture of the sleeve and before reentering the lumen through a second entrance aperture of the sleeve.

16. The prosthesis deployment system of claim 15, where, in the delivery state, the trigger wire further engages a third region of the at least one stent after extending out of the lumen through a third exit aperture of the sleeve and before reentering the lumen through a third entrance aperture of the sleeve.

\* \* \* \* \*

UNITED STATES PATENT AND TRADEMARK OFFICE
CERTIFICATE OF CORRECTION

PATENT NO. : 10,206,801 B2
APPLICATION NO. : 14/971222
DATED : February 19, 2019
INVENTOR(S) : Derek Eller Page 1 of 1

It is certified that error appears in the above-identified patent and that said Letters Patent is hereby corrected as shown below:

In the Claims

Column 6, Claim 10, Line 19, after "regions of the" delete second "the".

Signed and Sealed this
Twentieth Day of August, 2019

Andrei Iancu
*Director of the United States Patent and Trademark Office*